(12) United States Patent
Yamamoto

(10) Patent No.: US 7,250,589 B2
(45) Date of Patent: Jul. 31, 2007

(54) MICROWAVE HYPERTHERMIA TREATMENT APPARATUS AND TREATMENT SYSTEM

(75) Inventor: Ryuichi Yamamoto, Sapporo (JP)

(73) Assignee: Interlex Co., Ltd., Sapporo (JP)

( * ) Notice: Subject to any disclaimer, the term of this patent is extended or adjusted under 35 U.S.C. 154(b) by 10 days.

(21) Appl. No.: 11/161,928

(22) Filed: Aug. 23, 2005

(65) Prior Publication Data
US 2006/0049182 A1    Mar. 9, 2006

(30) Foreign Application Priority Data
Aug. 24, 2004    (JP)    ............... 2004-243935

(51) Int. Cl.
*H05B 6/64*    (2006.01)
*A61F 7/00*    (2006.01)

(52) U.S. Cl. .................... 219/678; 607/89; 607/156

(58) Field of Classification Search ................ 219/678, 219/686, 770, 679, 738, 759; 422/1, 21, 422/307; 128/898, 903, 904, 920; 600/411, 600/412, 439; 604/22; 606/41, 39, 45, 42; 607/99, 101, 116, 154, 89, 96, 113, 156, 104
See application file for complete search history.

(56) References Cited

U.S. PATENT DOCUMENTS

| 5,693,082 A * | 12/1997 | Warner et al. ............... 607/156 |
| 2005/0234530 A1* | 10/2005 | Takashino et al. ............ 607/89 |
| 2005/0251033 A1* | 11/2005 | Scarantino et al. ......... 600/436 |

* cited by examiner

*Primary Examiner*—Quang Van
(74) *Attorney, Agent, or Firm*—James W. Judge

(57) ABSTRACT

Microwave hyperthermia treatment device includes a microwave generation unit, a power supply unit, and a control unit including an exposure-time actuation timer, an intermittent actuation timer, a second-device connecting terminal, and a remote switch. Two microwave hyperthermia treatment devices are connected with each other via the second terminal connecting terminals for simultaneous use flanking the torso along either side of an affected area, whereby superposed strong microwaves are irradiated. The temperature of tumor(s) in the affected area can thereby be brought to about 43° C. in about 1 minute, rendering lengthy treatment periods unnecessary and thus alleviating temperature stress on the patient. Two remote-control switches to the control unit can be provided, one of which may be given to a patient for use as an emergency stop switch, eliminating the necessity of having to insert a temperature sensor in the body, which also alleviates the burden on the patient.

12 Claims, 8 Drawing Sheets

Step-up heating    Step-down heating

MICROWAVE HYPERTHERMIA TREATMENT APPARATUS AND TREATMENT SYSTEM

BACKGROUND OF THE INVENTION

1. Technical Field

The present invention relates to microwave-employing hyperthermia treatment devices and treatment systems.

2. Description of the Related Art

That a one-degree rise in human body temperature increases immunological competence by 30% is conventional knowledge, and a variety of thermotherapeutic techniques taking advantage of that fact are available. With microwave treatment devices, an extremely weak output is used for treating arthritis, chronic rheumatism, and similar diseases.

Achieving necrosis of cancerous tumors by putting the human body into hyperthermia of about 43° C. is also conventional knowledge. There are a variety of means by which the body can be put into hyperthermia, among which raising temperature by exposing the body to microwave energy is known.

A specific such example is in Japanese Unexamined Pat. App. Pub. No. S61-33668, in which an affected part of a patient's body is exposed to microwave energy at 2,450 MHz so as to continuously heat the affected part at about 43° C. for about an hour, and the process is repeated at regular intervals.

As an improvement in microwave hyperthermia techniques, Japanese Unexamined Pat. App. Pub. No. H05-23400 discloses an implementation comprising a first control means for controlling the number of microwave output pulses, and a second control means for controlling the output level.

This embodiment is configured such that microwave energy is output in synch with the power supply frequency, rendering the provision of a separate oscillator unnecessary. The number of pulses per second is changed by adjusting an output-adjusting dial. Accordingly, in the case of a 50 Hz commercial power supply, since the number of pulses output per second is 50, the per-second pulse count can be adjusted from 1 to 50 with the control dial.

As the dial is turned to make the adjusted output value greater, the number of microwave pulses output per second increases, along with which the wave height decreases. Conversely, as the dial is turned to make the adjusted output value smaller, the number of microwave pulses output per second decreases, along with which the wave height increases. Pat. App. Pub. No. H05-23400 states that accordingly, setting the output-adjusting dial to a low value enables a large dose of energy to be applied to biological tissue within a short period of time, whereby the biological tissue can be heated to deep-layer areas.

Further, the disclosed technique controls the microwave output energy with two control means so as to reduce the microwave output-power level along with an increase in the number of output pulses.

Meanwhile, Japanese Unexamined Pat. App. Pub. No. H08-206242 discloses technology for heating both deeper and surface areas by outputting microwave energy in intermittent pulses in alternation with a continuous pulse. This technology is embodied so as to output microwave energy in synch with the power supply frequency. Setting of the microwave output-power value per interval during which the microwave energy is output in intermittent pulses is done with pulsed-output count and power-level adjustments, and the setting per interval that the microwave energy is output in a continuous pulse is done with the power-level adjustment.

Therein, assuming that the ratio of the interval during which the microwave energy is output in intermittent pulses to the interval during which the microwave is output in a continuous pulse is 1:1 (=5 seconds:5 seconds), the disclosure teaches that in a 5-second period for the intermittent-pulse microwave output interval, five intermittent microwave pulses of 0.2 seconds pulse width are output with the power level being set to 500 watts, and in the ensuing 5-second period for the continuous-pulse microwave output interval, the power level is set to 100 watts.

In this conventional example, the output energy in the case of the intermittent pulses is 500 W×(0.2 s×5)=500 J, and the energy in the case of the continuous pulse is 100 W×5 s=500 J; thus the output energy of both the intermittent pulses and the continuous pulse is the same.

Since the output energy reaching an affected part is attenuated within a subject's body, with thus attenuated output energy levels, although it may be termed thermotherapy, the technology is unable to achieve necrosis of cancerous tumors.

In a still further example of hyperthermia treatment using microwave energy, Japanese Unexamined Pat. App. Pub. No. 2001-231870 discloses technology with a first oscillating means that outputs electromagnetic radiation at a first oscillation frequency, a second oscillating means that outputs electromagnetic radiation at a second oscillation frequency, and a mixing means that mixes and outputs simultaneously the electromagnetic radiation of the first and the second frequencies, wherein an affected area of a subject is exposed with the mixed-frequency electromagnetic radiation to heat the affected area.

In particular, high-frequency (2450 MHz) electromagnetic waves and low-frequency (915 MHz) electromagnetic waves differ in their tissue-depth attainment levels—that is, in their attenuation rates within tissue. Given that low-frequency electromagnetic radiation has a lower attenuation rate in tissue and can reach further than high-frequency electromagnetic radiation, electromagnetic waves at the two frequencies are mixed by the mixing means at a ratio of choice, and through an antenna section are irradiated onto the prostate area.

More specifically, with the technology disclosed in Pat. App. Pub. No. 2001-231870, the mixing ratio for the two frequencies of electromagnetic radiation is preset in accordance with the weight of the prostate. For example, if the prostate weighs less than 20 g, with 2450 MHz:915 MHz being a 9:1 ratio, and assuming a total output power of 50 W, then the proportions would be 45 W:5 W. Likewise, if the prostate weighs 40 to 50 g, with the ratio being 3:7 and assuming a the total output power of 50 W, the proportions would be 15 W:35 W.

Nevertheless, the conventional techniques discussed above each employ a single microwave treatment device and irradiate microwaves continuously for approximately one hour. Consequently, patients undergoing hyperthermia treatment must endure the high temperature for as long as an hour or so.

BRIEF SUMMARY OF THE INVENTION

An issue to be resolved by the present invention is that of a patient undergoing hyperthermia treatment having to endure for long periods high temperature that can distress the patient.

A microwave hyperthermia treatment device of the present invention is characterized mainly as to include a generation unit for generating microwaves, a power supply unit for driving the generation unit, and a control unit for controlling the power supply unit. The control unit includes an exposure-time actuation timer, an intermittent actuation timer, a second-device connecting terminal, and a remote switch connected with a remote-control cord.

The present invention is also characterized in that two remote switches can be provided if required.

When using, the present invention is characterized mainly in that two microwave hyperthermia treatment devices are connected via the second-device connecting terminals, enabling microwaves to be irradiated along both sides of an affected areas at the same time. Similarly, it is possible to connect four devices so as to use them at the same time while flanking two affected areas.

Further, if two remote switches are provided, one of them may be operated by the patient himself/herself.

A microwave hyperthermia treatment device of the present invention has a second-device connecting terminal, whereby two microwave treatment devices can be used by connecting them with each other. Therefore, by flanking the trunk along both sides of an affected area, a sufficient temperature rise can be achieved in a short period in the affected area, or inside a tumor in the body, with the superposed strong microwaves, while suppressing the temperature rise on the skin. Consequently, it is possible to reduce the period for the hyperthermia treatment.

Further, since the device includes an exposure-time actuation timer and an intermittent actuation timer, it is possible to adjust output, according to the object, from a high output to a low output by adjusting the intermittent actuation timer.

When it is adjusted to a high output, two microwave treatment devices are connected so as to irradiate superposed microwaves using powerful microwave output. This makes it possible to cause the temperature of the tumor of the affected part to be about 43° C. in about one to two minutes. Therefore, there is an advantage of reducing the burden on the patient since a long treatment period is not required.

When it is adjusted to a low output, it is possible to connect two microwave treatment devices for treating arthritis, chronic rheumatism or the like so as to irradiate microwaves from both directions onto an affected part. Further, four microwave treating devices may be connected to thereby treat both elbows, both knees or an elbow and a knee, at the same time.

Further, when two remote switches are provided, the patient may use one of them, whereby it can be used as an emergency stop switch when the patient himself/herself feels hot. Therefore, there is no need to insert a temperature sensor in the body for measuring the temperature of the affected part. This makes it possible to reduce the burden on the patient.

From the following detailed description in conjunction with the accompanying drawings, the foregoing and other objects, features, aspects and advantages of the present invention will become readily apparent to those skilled in the art.

DETAILED DESCRIPTION OF THE INVENTION

The object of remedying the shortcoming that a patient undergoing hyperthermia treatment must endure high temperature, causing trouble to the patient, for a long period, is realized with a simple configuration in which a control unit of a microwave hyperthermia treatment device includes an exposure-time actuation timer, an intermittent actuation timer, and a second-device connecting terminal, and further a remote switch connected to a remote-control cord is provided.

Further, two remote switches connected to remote-control cords may be provided if necessary.

Methods of microwave heating include the step-up method and the step-down method.

The former is also called step-up heating, and is a method of taking time to heat slowly, little by little. The latter is also called step down heating which is a method of heating rapidly.

In the case of step-up heating, it takes about 10 minutes or more to reach the object temperature. In contrast, in the case of step-down heating, it takes about 1 minute to reach the object temperature.

Further, in the case of step-up heating, since it takes time, heat-stable enzymes are generated inside the tumor. Therefore, step-down heating, with which rapid temperature increase is achievable, is desirable, considered in terms of the efficacy of treatment.

Figure 8:
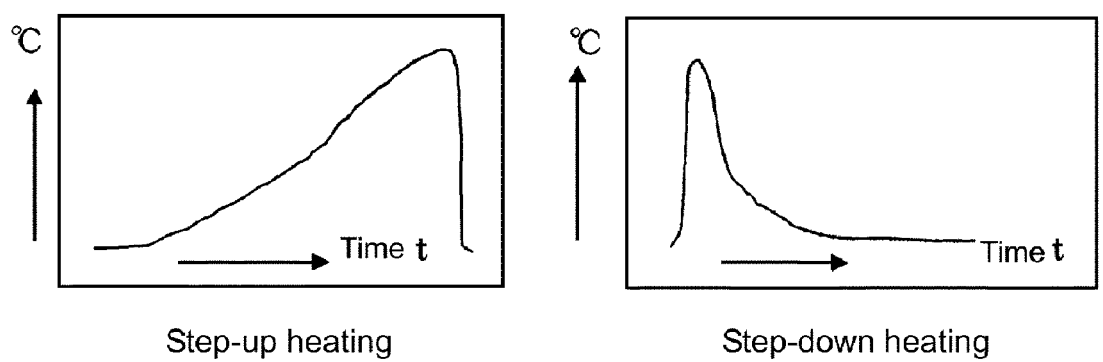
FIG. 8 is explanatory diagrams illustrating two heating methods for microwave heating.

FIG. 8 is graphs illustrating the two methods of microwave heating described above.

In the present invention, step-down heating of the step-down method is adopted.

Embodiment 1

Figure 1:
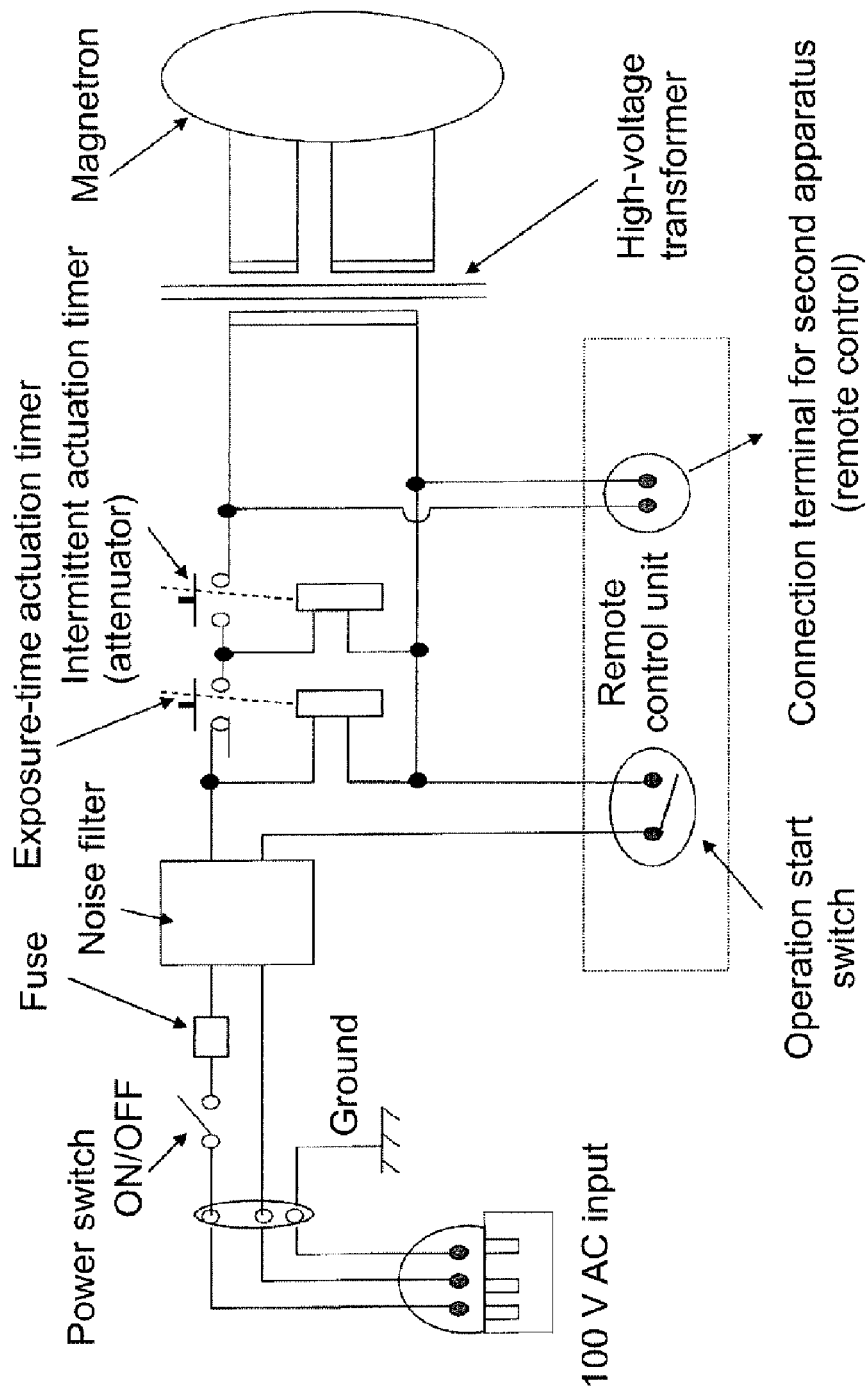
FIG. 1 is a block diagram showing the configuration of a microwave hyperthermia treatment device of Embodiment 1.
Figure 2:
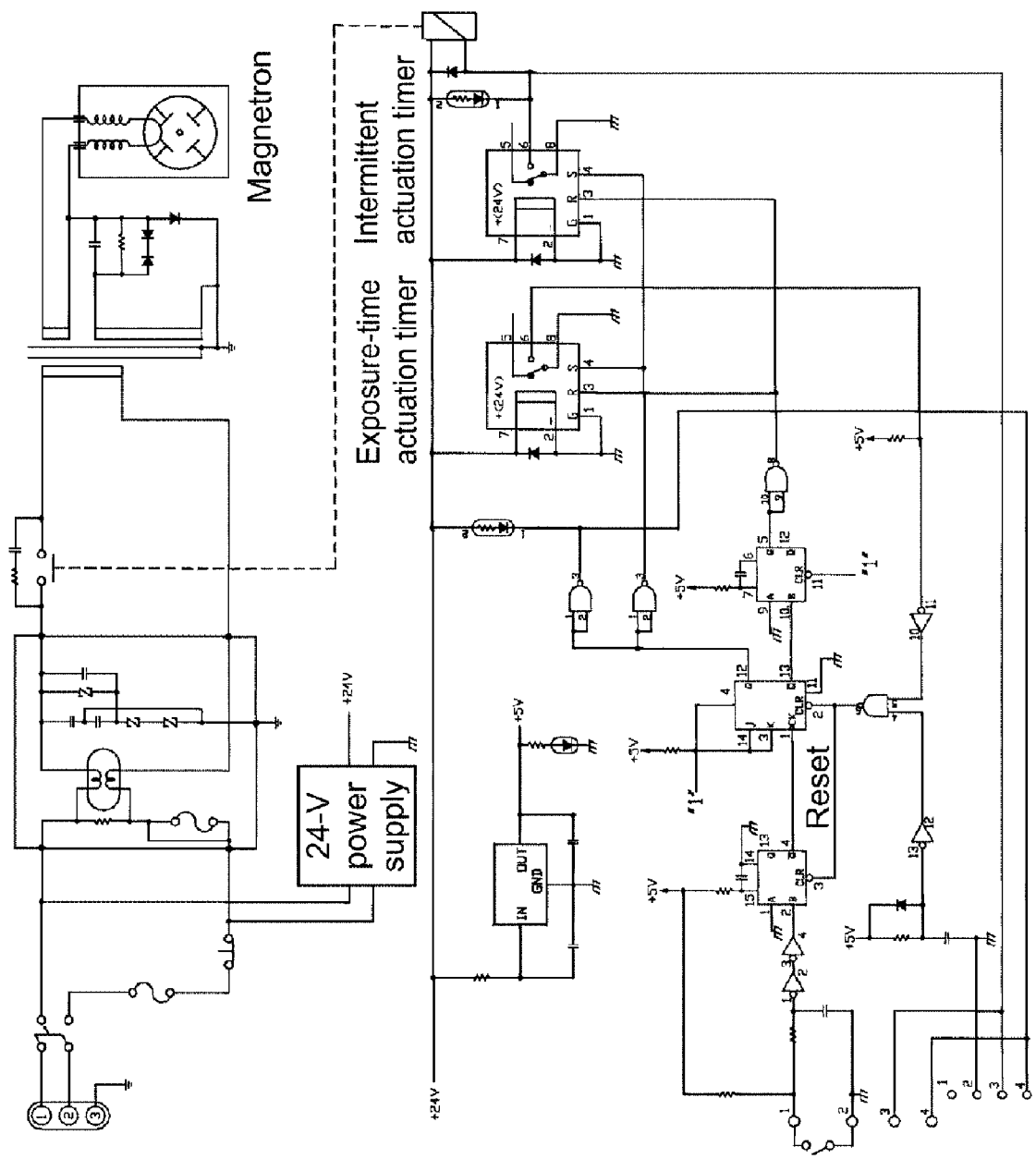
FIG. 2 is a circuit diagram of the microwave hyperthermia treatment device of Embodiment 1.

FIG. 1 is a block diagram showing an embodiment 1 of a microwave hyperthermia treatment device of the present invention. FIG. 2 is a circuit diagram of the microwave hyperthermia treatment device of the present invention.

The high-pressure transformer employed in Embodiment 1 is a well-known one, in which the primary side input is 100 V and the secondary side output is 4,000 V. Further, the magnetron employed is a well-known one, in which the frequency is 2,450 MHz and the rated output is 750 W.

The microwave hyperthermia treatment device unit 1 of the present invention is mounted on a swing mechanism 4 disposed on the upper part of a vertical mechanism 3 provided on a caster 2 with five legs.

Figure 3:
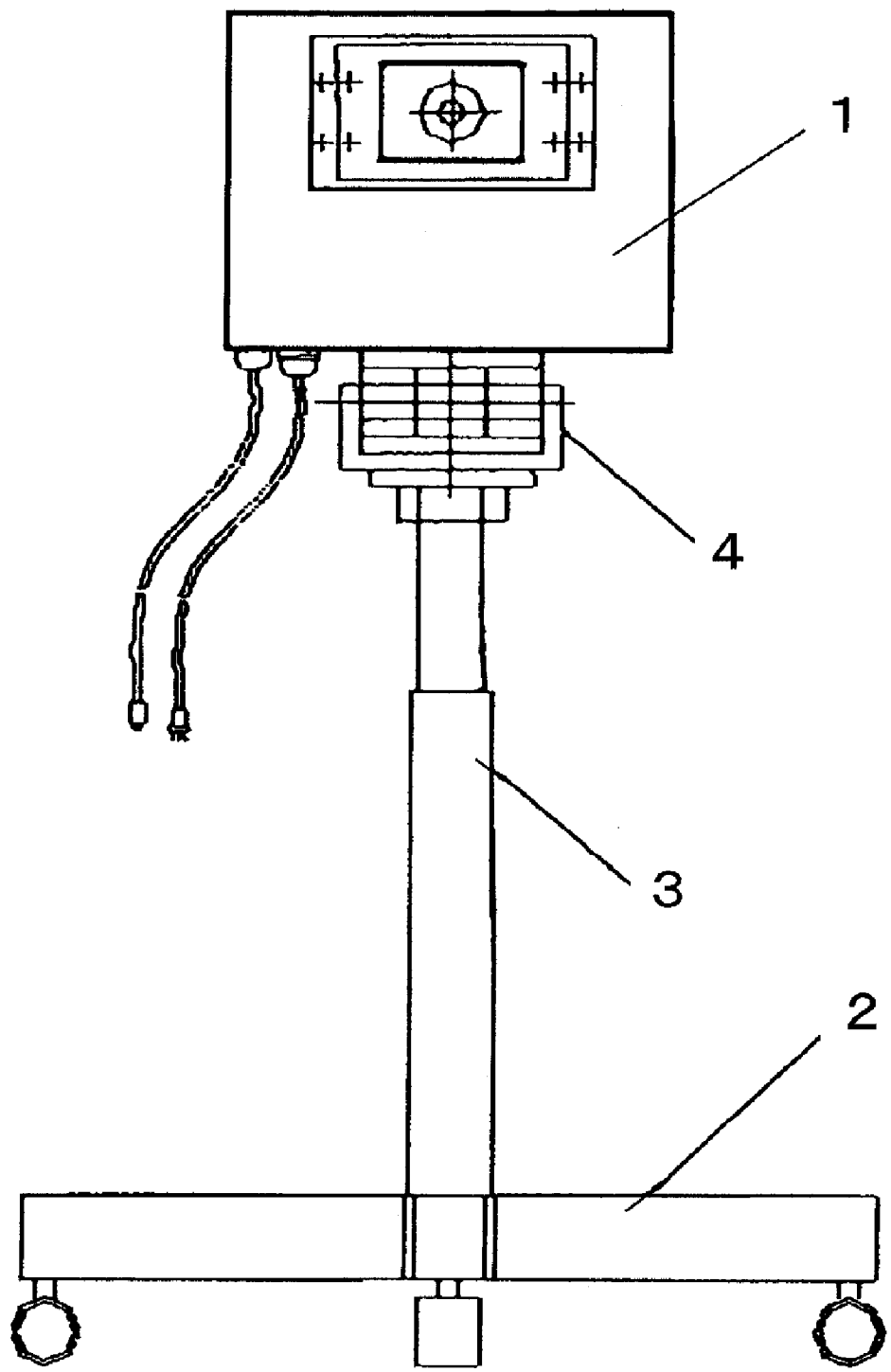
FIG. 3 is an elevational view of the microwave hyperthermia treatment device of Embodiment 1.

The configuration described above is shown in FIG. 3, as a front view of the microwave hyperthermia treatment device.

The swing mechanism 4 has a swing clamp 5, capable of moving the microwave hyperthermia treatment device unit 1 in vertical and horizontal directions. In Embodiment 1, the device unit 1 is movable up to 30° both up and down.

Figure 4:
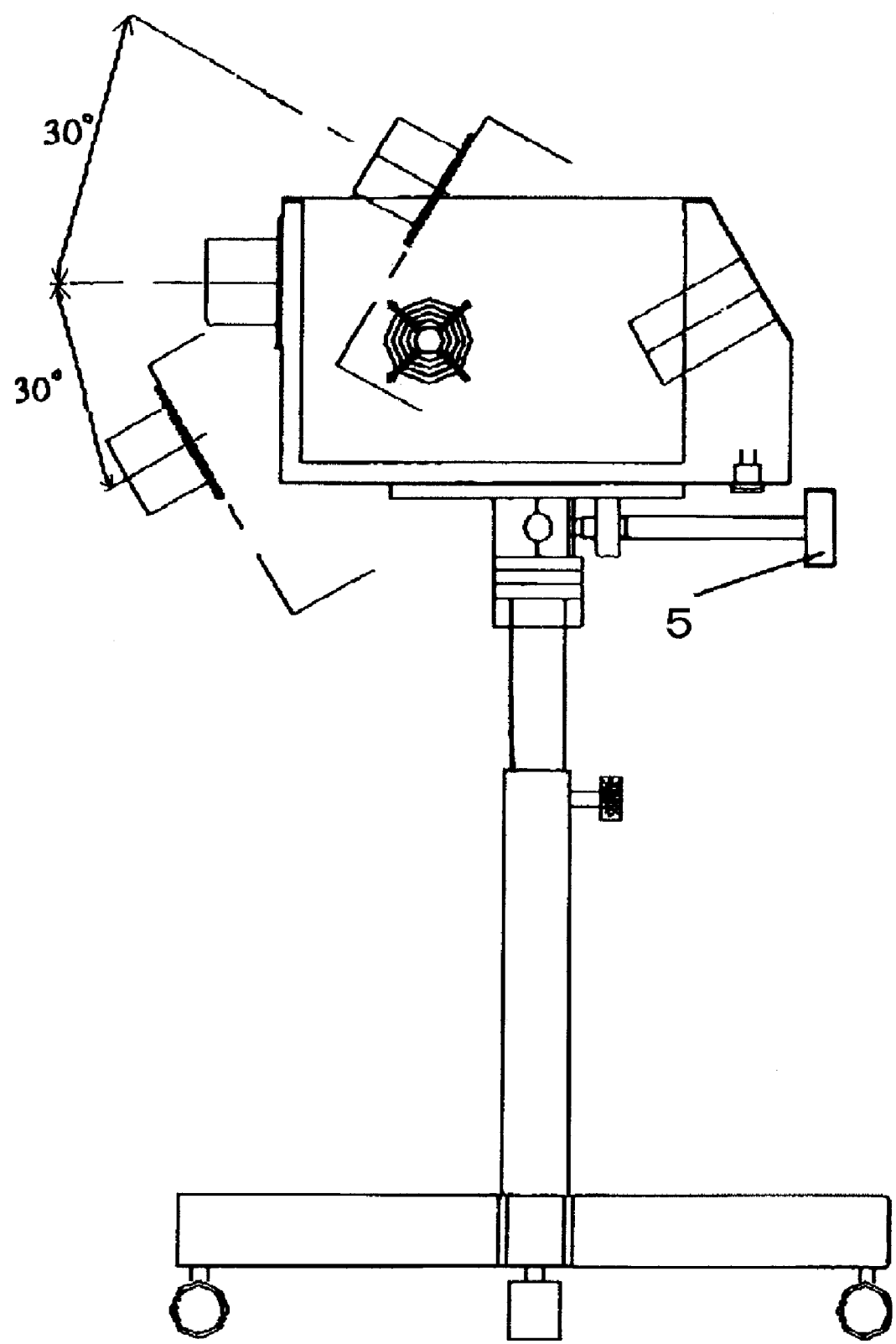
FIG. 4 is a lateral view of the microwave hyperthermia treatment device of Embodiment 1.

The configuration described above is shown in FIG. 4, as a side view of the microwave hyperthermia treatment device.

On the rear face of the microwave hyperthermia treatment device unit 1, there are provided an AC power supply switch 6, an operating panel 8 with which an exposure-time actuation timer 7 is set, and an operating panel 10 with which an intermittent actuation timer 9 is set, and a second-device connecting terminal 11.

On the lower face of the microwave hyperthermia treatment unit 1, there are provided an AC power supply cord 12, and a remote switch connected with a remote-control cord (operation start switch, stop switch) 13.

The configuration described above is shown in FIG. 5, as a rear view of the microwave hyperthermia treatment device.

Figure 5:
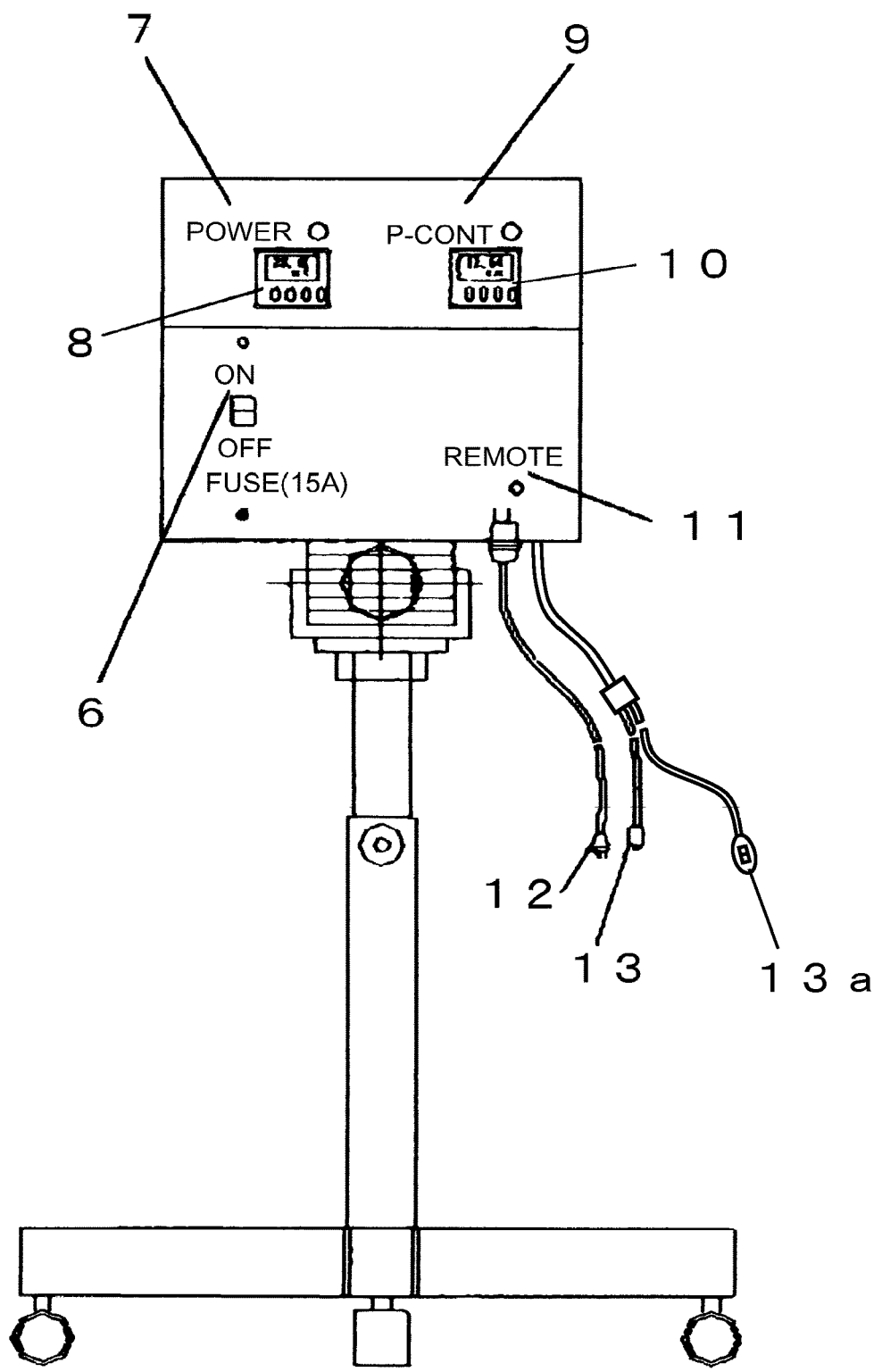
FIG. 5 is a rear view of the microwave hyperthermia treatment device of Embodiment 1.

As indicated in FIG. 5. two remote switches 13 and 13a may be provided if required, by being provided directly from the microwave hyperthermia treatment unit 1, or as FIG. 5 shows, split at the midway of the remote-control cord. The second remote switch 13a is an emergency stop switch for a patient, which is given to the patient. When the patient presses the switch when he/she feels hot, outputting of the microwave is emergently stopped. The second remote switch is so configured that the circuit will not start again even when the patient presses the switch button twice or more in haste.

The microwave hyperthermia treatment device outputs a microwave of 450 MHz with the maximum output of 750 W, which is capable of outputting a far stronger microwave than that of a conventional microwave treatment device.

Therefore, a sufficient temperature increase can be obtained in a short period, and the tumor temperature of the affected part reaches 43° C. in about 1 minute.

Figure 6:
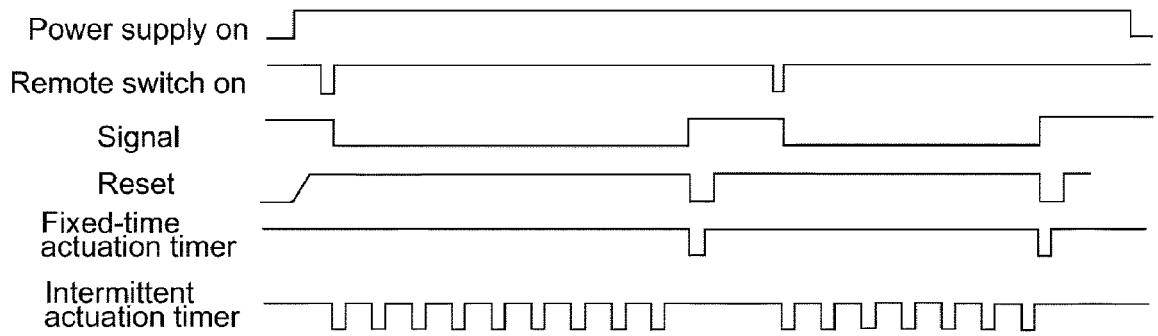
FIG. 6 is a timing chart diagramming control signals for the microwave hyperthermia treatment device of Embodiment 1.

FIG. 6 is a timing chart showing the control in the microwave hyperthermia treatment device.

The operating method of the microwave hyperthermia treatment device is as follows.

(1) Connect an AC power supply cord 12 to an AC 100 V plug socket (capacity 15 A).

(2) Set height and angle of the microwave hyperthermia treatment device to the intended position.

(3) Turn on the AC power supply switch 6 (lamp lighted).

(4) Set irradiating time period of the exposure-time actuation timer 7 with a setting switch of the operating panel 8. The set time is between 1 minute and 30 minutes, in 1-minute units.

(5) Set the exposure time period by the intermittent actuation timer 9 with a setting switch on the operating panel 10. Here, ON time and OFF time of the intermittent actuation timer 9 are set sequentially and independently.

The ON time of the intermittent timer 9 is set between 1 second and 30 seconds, in 1-second units.

The OFF time of the intermittent timer 9 is set between 0 second and 59 seconds, in 1-second units.

Assuming that the set time of the exposure-time actuation timer 7 is 10 minutes, the ON time of the intermittent actuation timer 9 is 10 seconds, and the OFF time is 5 seconds, for example, such a cycle is realized that it operates with a maximum output for 10 seconds, and is stopped for the next 5 seconds, and then operates with a maximum output for 10 seconds, for 10 minutes.

With this setting, the microwave hyperthermia treatment device of the present invention is capable of adjusting an output of 750 W maximum output with a microwave of 2,450 MHz frequency.

For example, the irradiation energy, in a case that the ON time is set to 3 seconds and the OFF time is set to 3 seconds, becomes an output equivalent to 50% of the maximum output of 750 W.

(6) Press the remote switch 13 at tip of the remote cable.

A lamp (red) of the exposure-time actuation timer 7 is lighted. Thereby, the operation of irradiating microwave starts, and intermittent irradiation is performed for the time period set by the exposure-time actuation timer 7 at intervals set by the intermittent actuation timer 9. During the period, the lamp (green) of the intermittent actuation timer 9 flashes.

(7) When the time period set by the exposure-time actuation timer 7 has passed, the lamp (red) of the exposure-time actuation timer 7 and the lamp (green) of the intermittent actuation timer 9 are extinct, and the irradiation of the microwave ends.

(8) In a case of halting the irradiation of the microwave during the operation, press the remote switch 13 at the tip of the remote cable again.

Further, if two remote switches 13 are provided, one remote switch 13a of them is given to the patient so as to be used as an emergency stop switch when the patients feels hot with an operation by the patient himself/herself.

Embodiment 2

Embodiment 2 is an example in which a connecting cable (not shown) is connected to the second-device connecting terminal 11 of the microwave hyperthermia treatment device of Embodiment 1 and the other end of the connecting cable is connected to a second-device connecting terminal 11 of a second microwave hyperthermia treatment device. The two devices are used at the same time so as to flank, along both sides of an affected area, a patient's torso.

The configuration described above is shown in FIG. 7A, as a schematic diagram showing in which the two microwave hyperthermia treatment devices of the present invention are used at the same time.

Figure 7A:
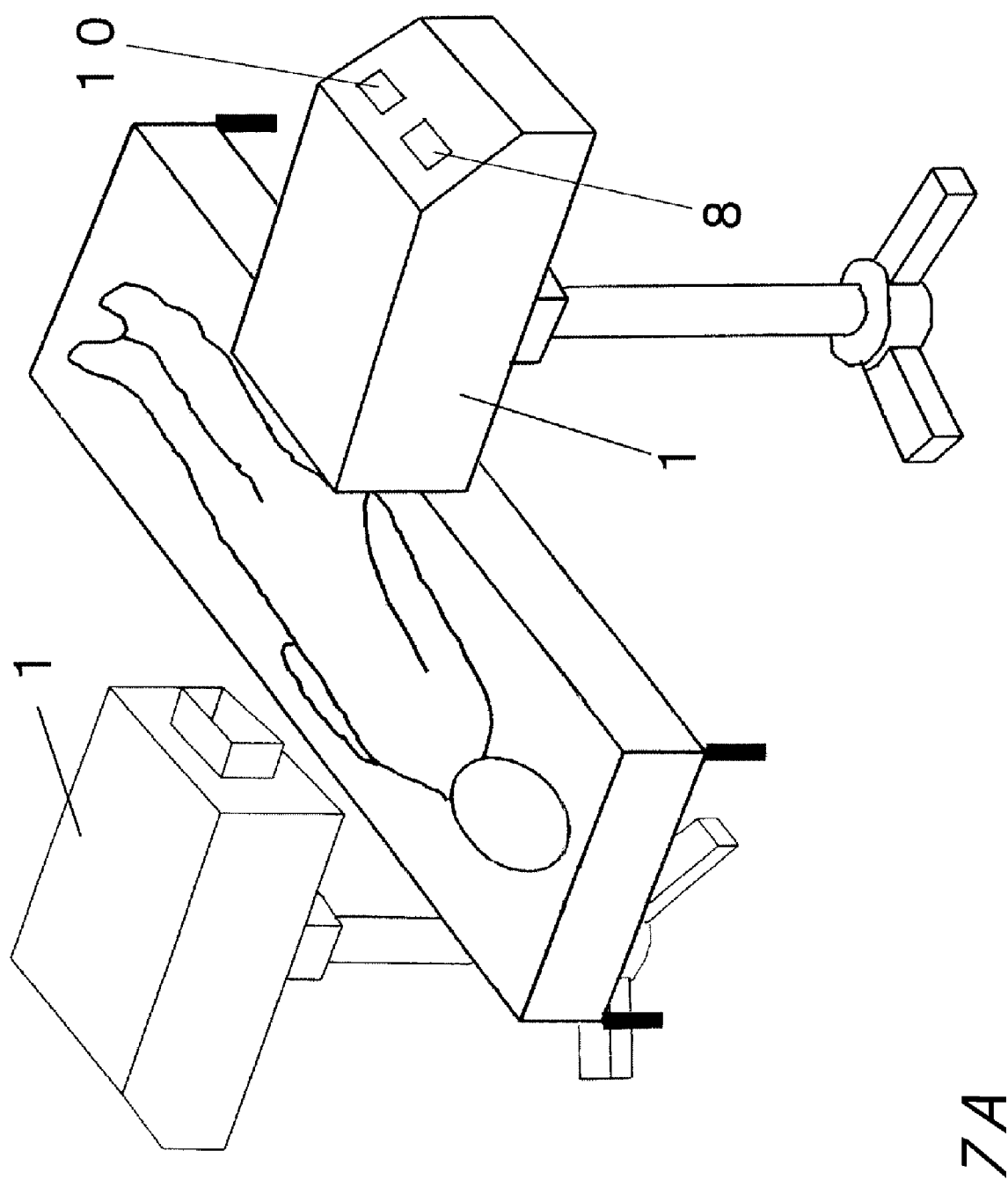
FIGS. 7A and 7B are schematic diagrams showing in Embodiments 2 and 3 respectively two and four microwave hyperthermia treatment devices connected via second-device connecting terminals on the microwave hyperthermia treatment devices for simultaneous use flanking, along both sides of an affected area, the torso of a patient.

The microwave irradiation angle in the case of using two microwave hyperthermia treatment devices of the present invention can be set to any angle within a range from about 90° to 180°. In FIG. 7A, they are used at 180° with the torso between them.

The operating method of using two microwave hyperthermia treatment devices connected via a connecting cable (not shown) is as follows.

(1) Connect the AC power supply cords 12 of the two microwave hyperthermia treatment devices to AC 100 V plug sockets (capacity 15 A).

(2) Set heights and angles of the two microwave hyperthermia treatment device to the intended positions.

(3) Set the exposure-time actuation timers 7 and the intermittent actuation timers 9 of the two devices to the same values.

(4) Connect the second-device connecting terminals 11 of the two microwave hyperthermia treatment devices with each other via a connecting cable (not shown).

(5) Press a remote switch 13 of one of the microwave hyperthermia treatment devices.

(6) Then, perform the same operation as that of the case of using one microwave hyperthermia treatment device.

As same as Embodiment 1, if two remote switches 13 are provided, one remote switch 13a of them is given to the patient so as to be used as an emergency stop switch when the patients feels hot with an operation by the patient himself/herself.

Further, given a setting example of the exposure-time actuation timer 7 and the intermittent actuation timer 9 and an operating method for reference, the set value of the exposure-time actuation timer 7 is 2 minutes, the set value of the ON time of the intermittent actuation timer 9 is 10 seconds, and the set value of the OFF time is 5 seconds.

The operating method automatically continues a cycle in which heating is performed for 10 seconds with microwaves with a rated output of 750 W, then heating is stopped for the next 5 seconds, and then heating is performed for the next 10 seconds (a time period from 15 seconds after the time when the remote switch 13 is first pressed to 25 seconds). During the period, if the patient says hot, the operation is stopped emergently with the remote switch 13, and while lowering the skin temperature during the quiescent period of 5 seconds, and the remote switch 13 is pressed again so as to repeat heating until the time period of the set value of the exposure-time actuation timer 7 is expired. If the remote switch 13a is given to the patient, the patient can stop the operation emergently by himself/herself with the remote switch 13a.

Further, if it is preferable to perform heating more carefully while watching the condition of the patient, setting the set value of the exposure-time actuation timer 7 to be 1 minute, the set value of the ON time of the intermittent actuation timer 9 to be 10 seconds, and the set value of the OFF time to be 0 seconds. Then, the operation of the remote switch 13 is performed manually every time so as to repeat the ON operation and the OFF operation, whereby an irradiation for 10 seconds can be realized with the maximum output energy.

The output energy of one device in this setting example is 750 W×10 s=7500 J. Since two devices are used with the torso between them, the total output energy is 7500 J ×2=15,000 J.

This equation indicates a comparison to the conventional example with the output energy.

The output energy is attenuated within the body and reaches the affected part, whereby the affected part (cancer tumor) itself generates thermal energy due to a dielectric loss effect to thereby cause necrosis of the cancer tumor.

When using two microwave hyperthermia treatment device at the same time by connecting with each other with high outputs, a coolant of various types such as a towel, a frozen pack, a thin ice bag, and a liquid circulation type cooling pack is applied to the skin surface, and a microwave is irradiated thereon.

This enables to prevent a possibility of a burn on the skin, and further the cancer tumor part within the body is heated sufficiently, whereby a necrosis effect of the cancer tissue can be obtained.

Embodiment 3

Figure 7B:
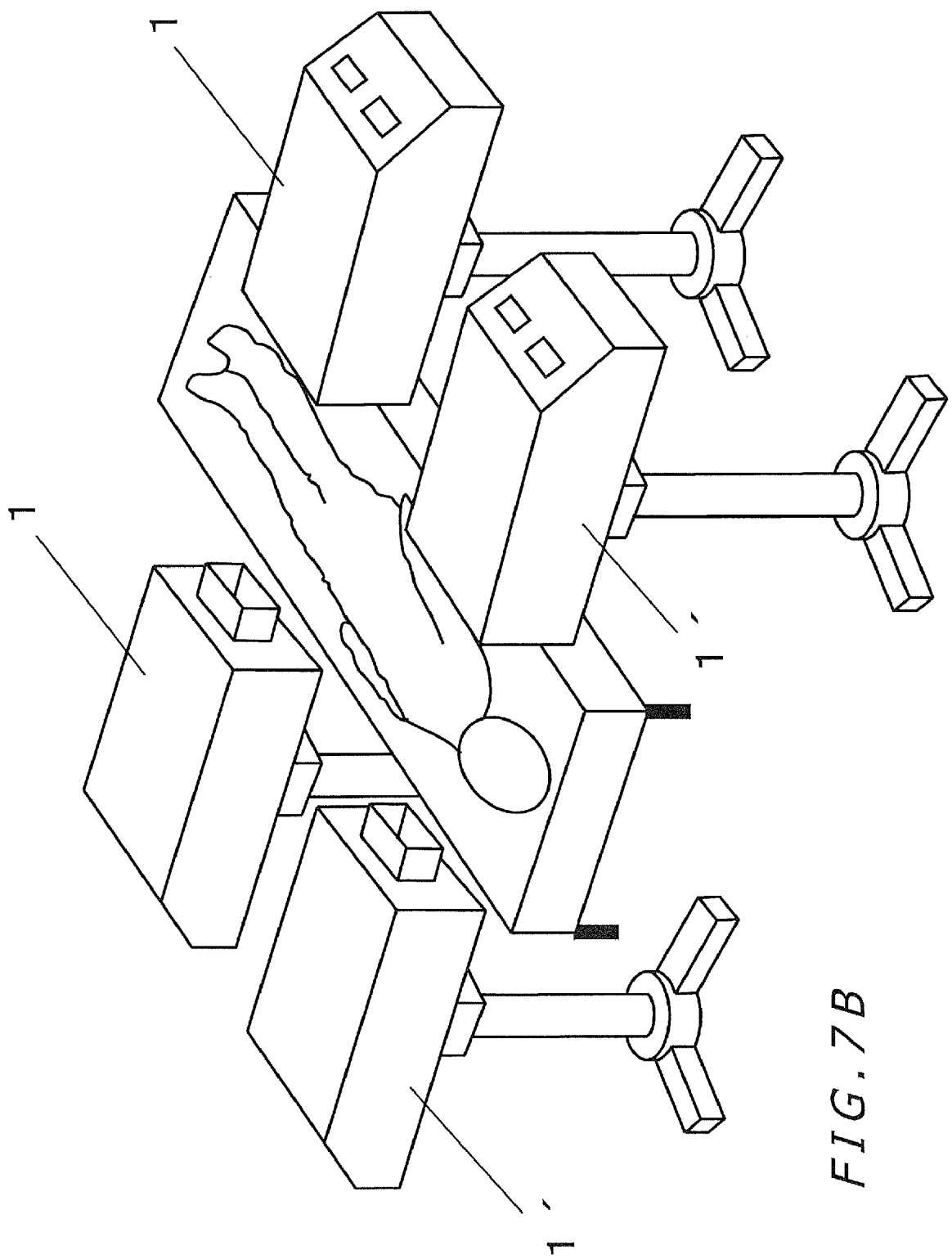

FIG. 7B shows an example in which a connecting cable (not shown) is connected to the second-device connecting terminal 11 of the microwave hyperthermia treatment device of Embodiment 1, and the other end of the connecting cable is connected with a second-device connecting terminal 11 of the second microwave hyperthermia treatment device, and a third microwave hyperthermia treatment device unit 1' and a forth microwave hyperthermia treatment device unit 1' are connected in series in the same manner to thereby use the four devices at the same time while flanking affected areas along both sides.

Given a setting example of the exposure-time actuation timer 7 and the intermittent actuation timer 9 and an operating method in the embodiment 3 for reference, the set value of the exposure-time actuation timer 7 is 30 minutes, the set value of the ON time of the intermittent actuation timer 9 is 1 second, and the set value of the OFF time is 15 seconds. In this setting example, the theoretical value of the average output in 16 seconds is equivalent to the output of 46.88 W.

The operating method automatically continues such a cycle for 30 minutes that heating is performed for 1 second with microwaves with a rated output of 750 W, then heating is automatically stopped for 15 seconds, and then heating is performed for the next 1 second. If the patient says he or she is hot, the operation is stopped emergently with the remote switch 13, and then heating is repeated until the time period of the set value of the exposure-time actuation timer 7 is expired.

If the remote switch 13a is given to the patient, the patient can stop emergently by himself/herself, in the same way as in Embodiments 1 and 2.

In the microwave hyperthermia treatment device using the conventional frequency of 2,450 MHz, those with 50 W output are typical, and none exceeding 500 W has been known. This is because harmful effects and dangerousness, in particular, the risk of burns due to high-output-power electromagnetic radiation, are concerns. Therefore, it has been a common knowledge that heating by the step-up method in which heating is performed slowly while taking sufficient time brings a sufficient effect.

The present invention has been developed based on the knowledge that the reason described above is a common knowledge lacking in scientific basis, and no one had been tried, and a short time exposure for treatment is harmless. Thereby, a microwave hyperthermia treatment device with a high output of 750 W has been developed.

Further, with a second-device connecting terminal 11, not only one but also a plurality of devices can be used at the same time, and by flanking an affected area along both sides of the torso, a sufficient temperature rise can be achieved in the affected part or in the tumor part of the body in a short period while suppressing the temperature increase in the skin. Further, since the device can be used for treating a plurality of affected parts at the same time, the application becomes wider.

Further, since two remote switches 13 can be provided if required, one of them may be given to a patient so as to be used as an emergency stop switch when the patient feels hot with an operation by the patient himself/herself. Therefore, there is no need to insert a temperature sensor within the body for measuring the temperature of an affected part.

Only selected embodiments have been chosen to illustrate the present invention. To those skilled in the art, however, it will be apparent from the foregoing disclosure that various changes and modifications can be made herein without departing from the scope of the invention as defined in the appended claims. Furthermore, the foregoing description of the embodiments according to the present invention is provided for illustration only, and not for limiting the invention as defined by the appended claims and their equivalents.

What is claimed is:

1. A microwave hyperthermia treatment device comprising:
   a generation unit for generating microwaves;
   a power supply unit for driving the generation unit; and
   a control unit for controlling the power supply unit, the control unit including
      an exposure-time actuation timer,
      an intermittent actuation timer,
      a second-device connecting terminal, and
      a remote switch connected to a remote-control cord.

2. A microwave hyperthermia treatment device comprising:
   a generation unit for generating microwaves;
   a power supply unit for driving the generation unit; and
   a control unit for controlling the power supply unit, the control unit including
      an exposure-time actuation timer,
      an intermittent actuation timer,
      a second-device connecting terminal, and
      two remote switches connected to a remote-control cord.

3. The microwave hyperthermia treatment device as set forth in claim 1, wherein the generation unit for generating microwaves has a rated output of 750 W at 2,450 MHz.

4. The microwave hyperthermia treatment device as set forth in claim 2, wherein the generation unit for generating microwaves has a rated output of 750 W at 2,450 MHz.

5. A microwave hyperthermia treatment system wherein two microwave hyperthermia treatment devices according to claim 1 are connected via the second-device connecting terminals for simultaneous use flanking the torso of a patient along both sides of an affected area.

6. A microwave hyperthermia treatment system wherein two microwave hyperthermia treatment devices according to claim 2 are connected via the second-device connecting terminals for simultaneous use flanking the torso of a patient along both sides of an affected area.

7. A microwave hyperthermia treatment system wherein two microwave hyperthermia treatment devices according to claim 3 are connected via the second-device connecting terminals for simultaneous use flanking the torso of a patient along both sides of an affected area.

8. A microwave hyperthermia treatment system wherein two microwave hyperthermia treatment devices according to claim 4 are connected via the second-device connecting terminals for simultaneous use flanking the torso of a patient along both sides of an affected area.

9. A microwave hyperthermia treatment system wherein four microwave hyperthermia treatment devices according to claim 1 are connected via the second-device connecting terminals for simultaneous use flanking the torso of a patient along both sides of two affected areas.

10. A microwave hyperthermia treatment system wherein four microwave hyperthermia treatment devices according to claim 2 are connected via the second-device connecting terminals for simultaneous use flanking the torso of a patient along both sides of two affected areas.

11. A microwave hyperthermia treatment system wherein four microwave hyperthermia treatment devices according to claim 3 are connected via the second-device connecting terminals for simultaneous use flanking the torso of a patient along both sides of two affected areas.

12. A microwave hyperthermia treatment system wherein four microwave hyperthermia treatment devices according to claim 4 are connected via the second-device connecting terminals for simultaneous use flanking the torso of a patient along both sides of two affected areas.

* * * * *